United States Patent
Horng (10) Patent No.: US 9,452,373 B1
(45) Date of Patent: Sep. 27, 2016

(54) FILTER FUNNEL FOR CONNECTION TO FLASK

(71) Applicant: Rock Scientific Co., Ltd., Kaohsiung (TW)

(72) Inventor: Shui-Tien Horng, Kaohsiung (TW)

(73) Assignee: ROCKER SCIENTIFIC CO., LTD., Kaohsiung (TW)

( * ) Notice: Subject to any disclaimer, the term of this patent is extended or adjusted under 35 U.S.C. 154(b) by 0 days.

(21) Appl. No.: 14/699,814

(22) Filed: Apr. 29, 2015

(51) Int. Cl.
*B01D 29/085* (2006.01)
*B01D 29/05* (2006.01)
*G01N 1/40* (2006.01)

(52) U.S. Cl.
CPC ............ *B01D 29/05* (2013.01); *B01D 29/085* (2013.01); *B01D 2201/204* (2013.01); *B01L 2300/0681* (2013.01); *G01N 2001/4088* (2013.01)

(58) Field of Classification Search
None
See application file for complete search history.

(56) References Cited

U.S. PATENT DOCUMENTS

| | | | |
|---|---|---|---|
| 3,831,759 A * | 8/1974 | Gelman ................. | B01D 23/28 210/232 |
| 3,838,978 A * | 10/1974 | Eddleman .............. | B01D 23/28 210/406 |
| 4,301,010 A | 11/1981 | Eddleman et al. | |
| 4,468,321 A * | 8/1984 | St. John ................. | B01D 29/05 210/232 |
| 4,890,484 A * | 1/1990 | Telfer ...................... | G01N 1/28 73/61.72 |
| 5,217,619 A * | 6/1993 | Redmond, Jr. .... | B01D 11/0219 210/321.75 |
| 2004/0188344 A1* | 9/2004 | Scott ...................... | B01D 61/16 210/406 |
| 2005/0189290 A1 | 9/2005 | Maiden | |
| 2009/0236341 A1 | 9/2009 | Mckinney et al. | |

FOREIGN PATENT DOCUMENTS

| EP | 0900174 A2 | 3/1999 |
|---|---|---|
| TW | I 300008 B | 8/2008 |
| TW | M475283 U | 4/2014 |
| WO | WO 01/16029 A1 | 3/2001 |

* cited by examiner

*Primary Examiner* — Thomas M Lithgow
(74) *Attorney, Agent, or Firm* — Muncy, Geissler, Olds & Lowe, P.C.

(57) ABSTRACT

A filter funnel has a funnel seat, a tubular stem, and a seal washer that is sleeved on the tubular stem and abuts against an abutment region of the funnel seat. The seal washer has a slot registering with a port of a vacuum intake duct formed in the funnel seat and is disposed to cover an access opening of a flask. When the flask is connected to a vacuum source through the vacuum intake duct to create reduced pressure in the flask, the seal washer presses against a flask neck of the flask to provide an air-tight seal between the access opening and the slot, thereby facilitating flowing of a liquid fraction of a mixture introduced into the filter funnel into the flask.

9 Claims, 8 Drawing Sheets

FILTER FUNNEL FOR CONNECTION TO FLASK

FIELD

The disclosure relates to a filter funnel, more particularly to a filter funnel for connection to a flask.

BACKGROUND

U.S. Pat. No. 4,301,010 discloses a conventional vacuum filter funnel which is useful for separating solids from liquids. The funnel has a vacuum intake member which forms an airtight seal with a filtrate container, and also forms an airtight seal with an upper funnel member which has a perforated bottom. A threaded sleeve member fits within the upper funnel member and assists in holding the filter medium above the perforated bottom.

However, because the vacuum intake member has a bottom outlet shaped to form an airtight seal with the filtrate container, a neck of the filtrate container needs to be of a specific size. In addition, if it is necessary to separate solids and liquids of a large volume, it would be troublesome to replace a filled filtrate container with an empty one.

SUMMARY

Therefore, an object of the disclosure is to provide a filter funnel which can be easily connected to flasks with different flask neck sizes.

According to the disclosure, a filter funnel for connection to a flask includes a funnel seat, a funnel surrounding wall, a tubular stem, and a seal washer. The flask has a flask body defining an interior chamber therein, and a flask neck that has an access opening in fluid communication with the interior chamber. The funnel seat has upper and lower surfaces, a through hole, an outer peripheral surface, and a vacuum intake duct. The upper surface defines a central line and has a central surface region and a marginal surface region surrounding the central surface region. The lower surface is formed with a recess which extends from the lower surface along the central line toward the upper surface to terminate at an abutment region. The lower surface and the abutment region define therebetween an inner surrounding surface which surrounds the central line. The through hole extends along the central line and downwardly from the central surface region to the abutment region. The outer peripheral surface is configured to surround the central line and to join the upper surface with the lower surface, and has a vacuum intake port. The vacuum intake duct extends radially from the vacuum intake port to terminate at an internal port which is in fluid communication with the interior chamber of the flask body. The funnel surrounding wall is disposed on the marginal surface region of the upper surface of the funnel seat to define an accommodation space for introducing a mixture to be filtered. The tubular stem extends downwardly from the abutment region, and is coaxial with and in fluid communication with the through hole so as to permit the through hole to be in fluid communication with the interior chamber of the flask body. The seal washer has a through bore and a slot. The through bore is configured to permit the seal washer to be sleeved on the tubular stem so as to allow the seal washer to be brought to an attached position where the seal washer abuts against the abutment region. The slot is configured to register with the internal port when the seal washer is in the attached position such that when the seal washer is brought to cover the access opening, and when the vacuum intake port is connected to a source of vacuum, a reduced pressure is created in the interior chamber of the flask body to enable the seal washer to press against the flask neck, thereby providing an air-tight seal between the access opening and the slot.

BRIEF DESCRIPTION OF THE DRAWINGS

Other features and advantages of the disclosure will become apparent in the following detailed description of the embodiments of the invention, with reference to the accompanying drawings, in which.

DETAILED DESCRIPTION

Before the disclosure is described in greater detail, it should be noted that like elements are denoted by the same reference numerals throughout the disclosure.

Figure 1:
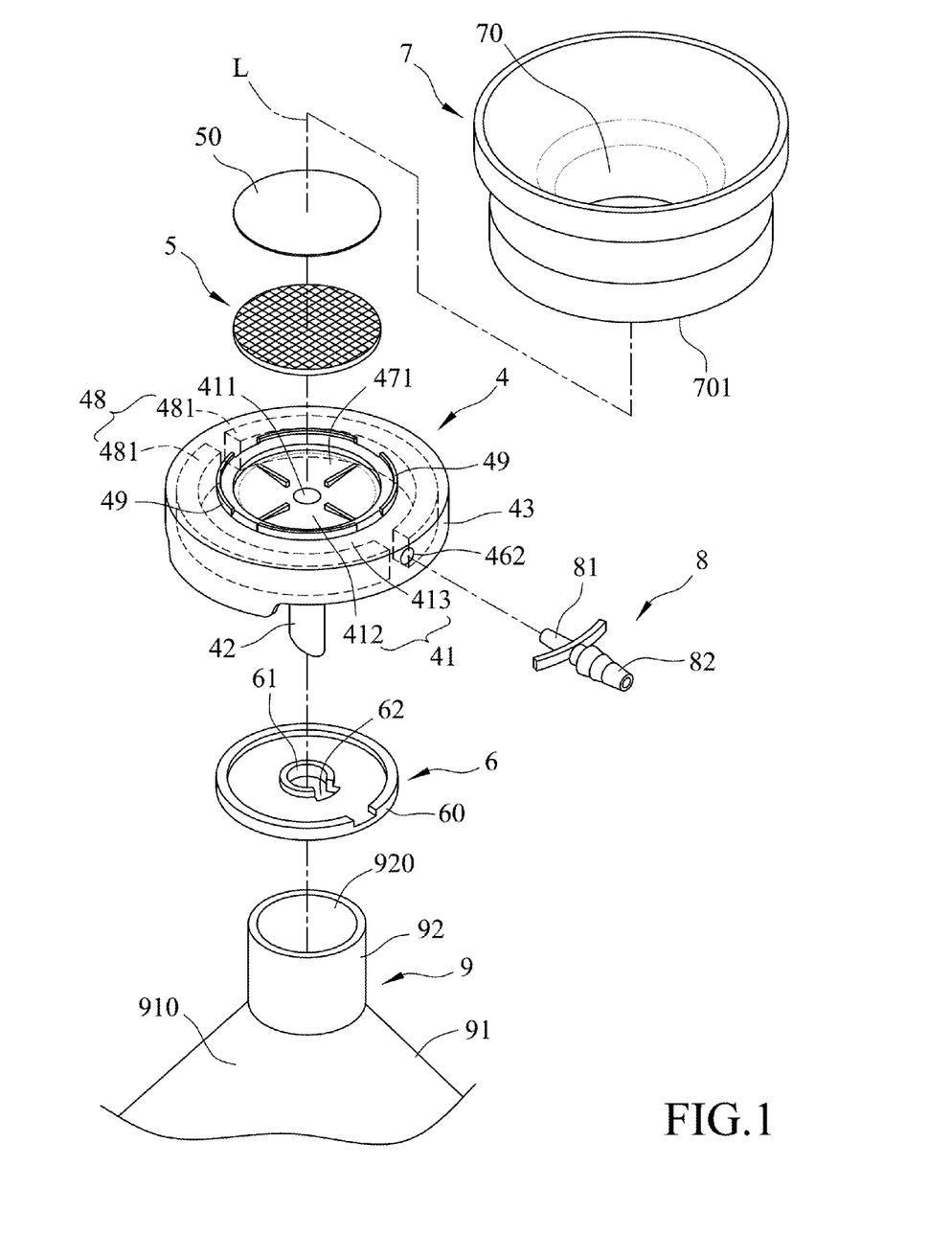
FIG. 1 is an exploded perspective view of a first embodiment of a filter funnel according to the disclosure.
Figure 2:
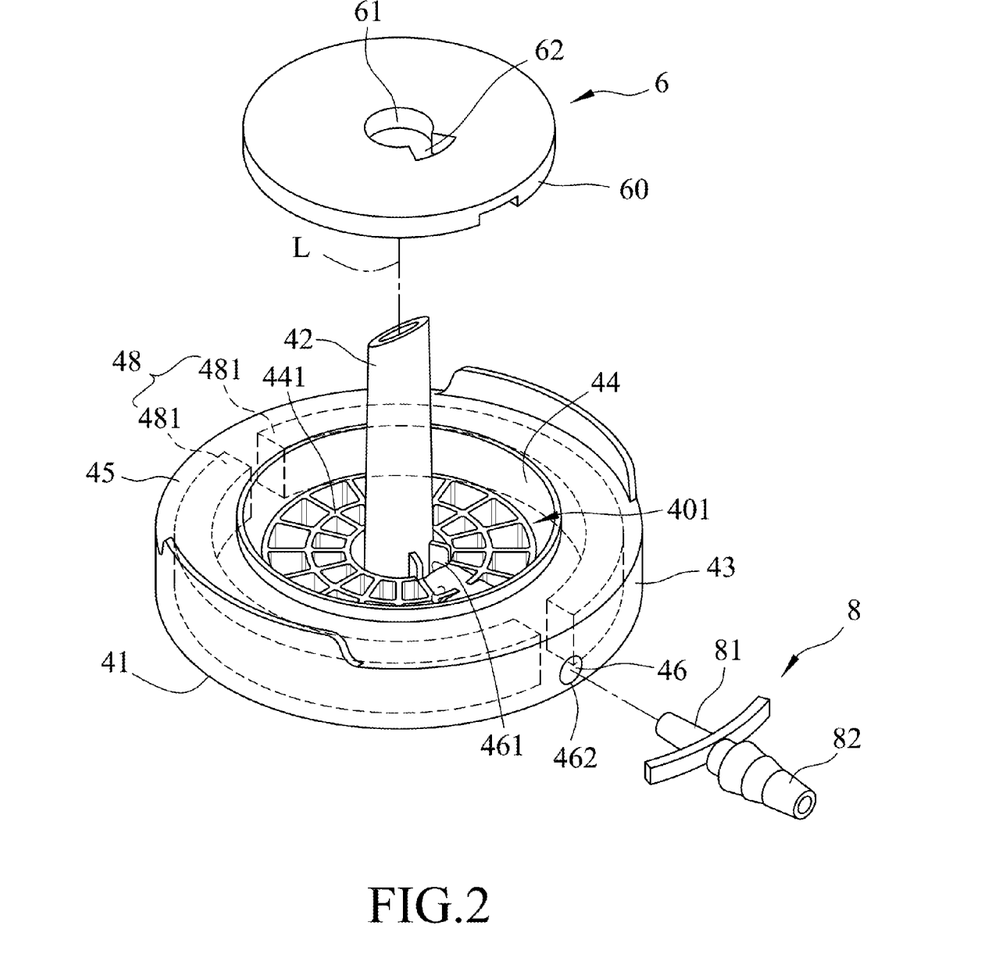
FIG. 2 is an exploded perspective view of a funnel seat, a tubular stem, a seal washer, and a tubular connector of the filter funnel of FIG. 1 taken from another angle.

Referring to FIGS. 1 and 2, a first embodiment of a filter funnel according to the disclosure is shown to include a funnel seat 4, a seal washer 6, a funnel surrounding wall 7, and a tubular stem 42. The filter funnel is used for connection to a flask 9, especially a thick-walled Erlenmeyer flask, which has a strength sufficient to withstand the pressure difference while holding a vacuum inside. Generally, the flask 9 has a flask body 91 and a flask neck 92. The flask body 91 defines an interior chamber 910 therein. The flask neck 92 has an access opening 920 in fluid communication with the interior chamber 910. A filter paper 50 can be placed in the filter funnel to separate a solid fraction of a mixture introduced into the filter funnel from a liquid fraction of the mixture.

The funnel seat 4 has upper and lower surfaces 41, 45, a through hole 411, an outer peripheral surface 43, and a vacuum intake duct 46.

The upper surface 41 defines a central line (L) and has a central surface region 412 and a marginal surface region 413. The marginal surface region 413 surrounds the central surface region 412.

As best shown in FIG. 2, the lower surface 45 is formed with a recess 401 which extends from the lower surface 45 along the central line (L) toward the upper surface 41 to terminate at an abutment region 441. The lower surface 45 and the abutment region 441 define therebetween an inner surrounding surface 44 which surrounds the central line (L).

Figure 3:
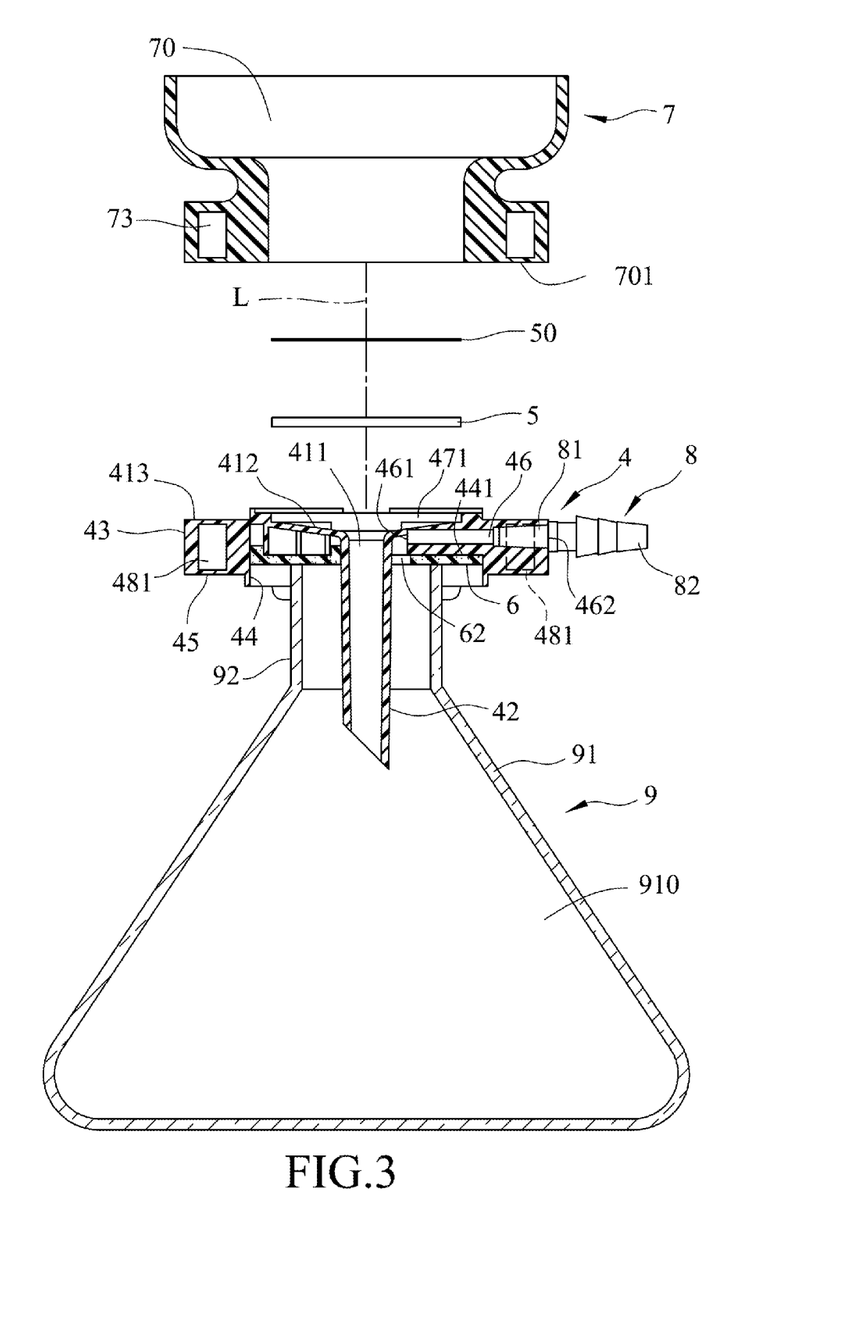
FIG. 3 is a partially cross-sectional view of the filter funnel shown in FIG. 1, in which a funnel surrounding wall is detached from the funnel seat.

The through hole 411 extends along the central line (L) and downwardly from the central surface region 412 to the abutment region 441 (see also FIG. 3). Referring back to FIG. 1, in this embodiment, the central surface region 412 is shown to have a plurality of guide paths 471 each of which extends from the marginal surface region 413 and is downwardly inclined toward the through hole 411.

The outer peripheral surface 43 is configured to surround the central line (L) and to join the upper surface 41 with the lower surface 45, and has a vacuum intake port 462.

As best shown in FIG. 3, the vacuum intake duct 46 extends radially from the vacuum intake port 462 to terminate at an internal port 461 which is in fluid communication with the interior chamber 910 of the flask body 91. The internal port 461 is disposed in the recess 401.

The funnel surrounding wall 7 is disposed on the marginal surface region 413 of the upper surface 41 of the funnel seat 4 to define an accommodation space 70 for introducing a mixture to be filtered. The funnel surrounding wall 7 has a bottom surrounding end surface 701 which is detachably attached to the marginal surface region 413 of the upper surface 41 of the funnel seat 4.

In this embodiment, a first magnetically attractive member 73, which is annular in shape, is embedded in the bottom surrounding end surface 701 of the funnel surrounding wall 7 (see FIG. 3), and a second magnetically attractive member 48 is embedded in the marginal surface region 413 of the upper surface 41 of the funnel seat 4. At least one of the first and second magnetically attractive members 73, 48 is a magnet. When the bottom surrounding end surface 701 of the funnel surrounding wall 7 is attached to the marginal surface region 413 of the upper surface 41 of the funnel seat 4, the bottom surrounding end surface 701 and the marginal surface region 413 are sealed by means of a magnetic attractive force generated between the first and second magnetically attractive members 73, 48. As shown in FIG. 1, the second magnetically attractive member 48 includes two half portions 481 which are respectively embedded in left and right halves of the marginal surface region 413.

In this embodiment, the funnel seat 4 further has a plurality of rib portions 49 which are displaced from each other in a circumferential direction, and are disposed between the central surface region 412 and the marginal surface region 413 to permit the rib portions 49 to be fitted in and to be surrounded by the funnel surrounding wall 7.

The tubular stem 42 extends downwardly from the abutment region 441, and is coaxial with and in fluid communication with the through hole 411 so as to permit the through hole 411 to be in fluid communication with the interior chamber 910 of the flask body 91.

The seal washer 6 is made of an elastomeric material, and has a through bore 61, a slot 62, and a peripheral edge 60. The through bore 61 is configured to permit the seal washer 6 to be sleeved on the tubular stem 42 so as to allow the seal washer 6 to be brought to an attached position where the seal washer 6 abuts against the abutment region 441. The slot 62 is configured to register with the internal port 461 when the seal washer 6 is in the attached position such that when the seal washer 6 is brought to cover the access opening 920, and when the vacuum intake port 462 is connected to a source of vacuum, a reduced pressure is created in the interior chamber 910 of the flask body 91 to enable the seal washer 6 to press against the flask neck 92, thereby providing an air-tight seal between the access opening 920 and the slot 62. The source of vacuum may be an aspirator, a vacuum pump, a house vacuum, etc. In this embodiment, the slot 62 extends radially to communicate with the through bore 61.

In addition, when the seal washer 6 is in the attached position, the peripheral edge 60 is engaged with the inner surrounding surface 44.

As shown in FIGS. 1 and 3, a mesh disc 5 is detachably disposed above the guide paths 471, for supporting the filter paper 50.

The filter funnel further includes a tubular connector 8 including a plug end 81 and a coupling end 82. The plug end 81 is configured to be plugged into the vacuum intake duct 46 to close the vacuum intake port 462. The coupling end 82 is connected to the source of vacuum. After the mixture (not shown) to be filtered is introduced into the accommodation space 70 and the coupling end 82 is connected to the source of vacuum to create a reduced pressure in the interior chamber 910, a liquid fraction 900 of the mixture (see FIG. 4 or 5) flows into the interior chamber 910 due to the pressure difference between the interior chamber 910 and the accommodation space 70.

Figure 4:
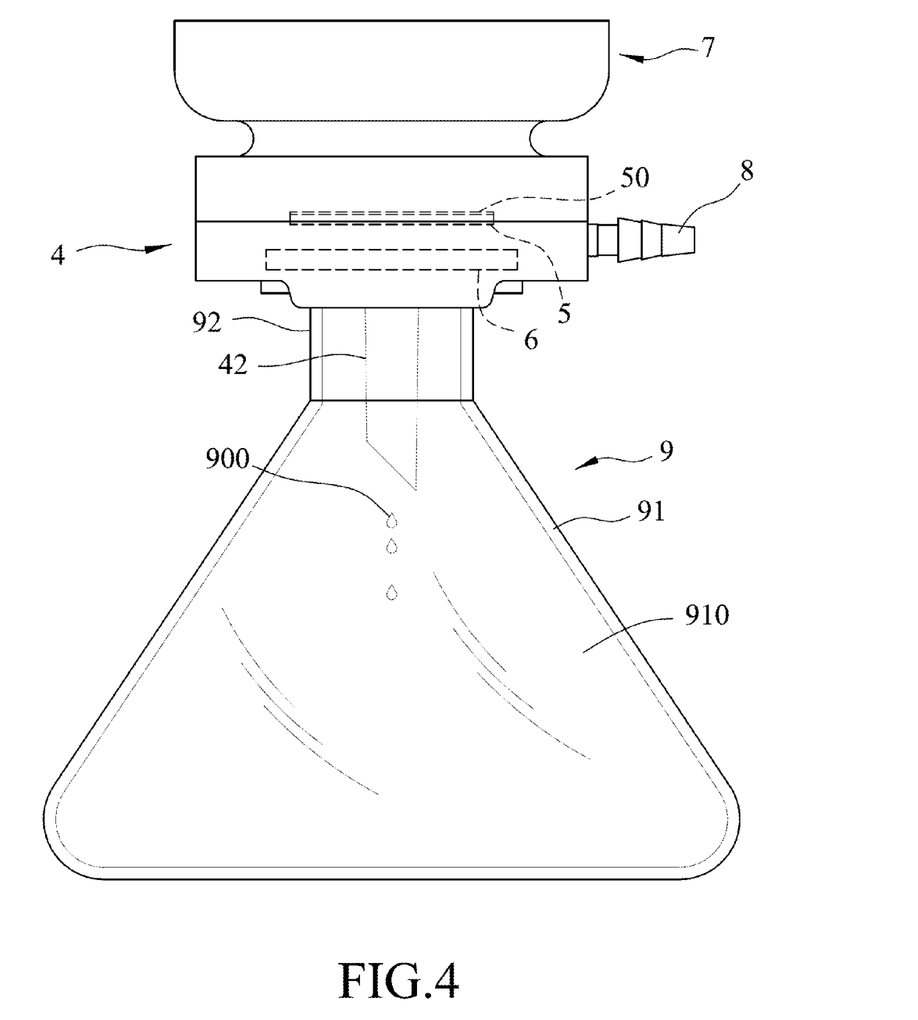
FIG. 4 is a side view of the filter funnel of FIG. 1, which is in an assembled state, and which is connected to a wide-neck flask.
Figure 5:
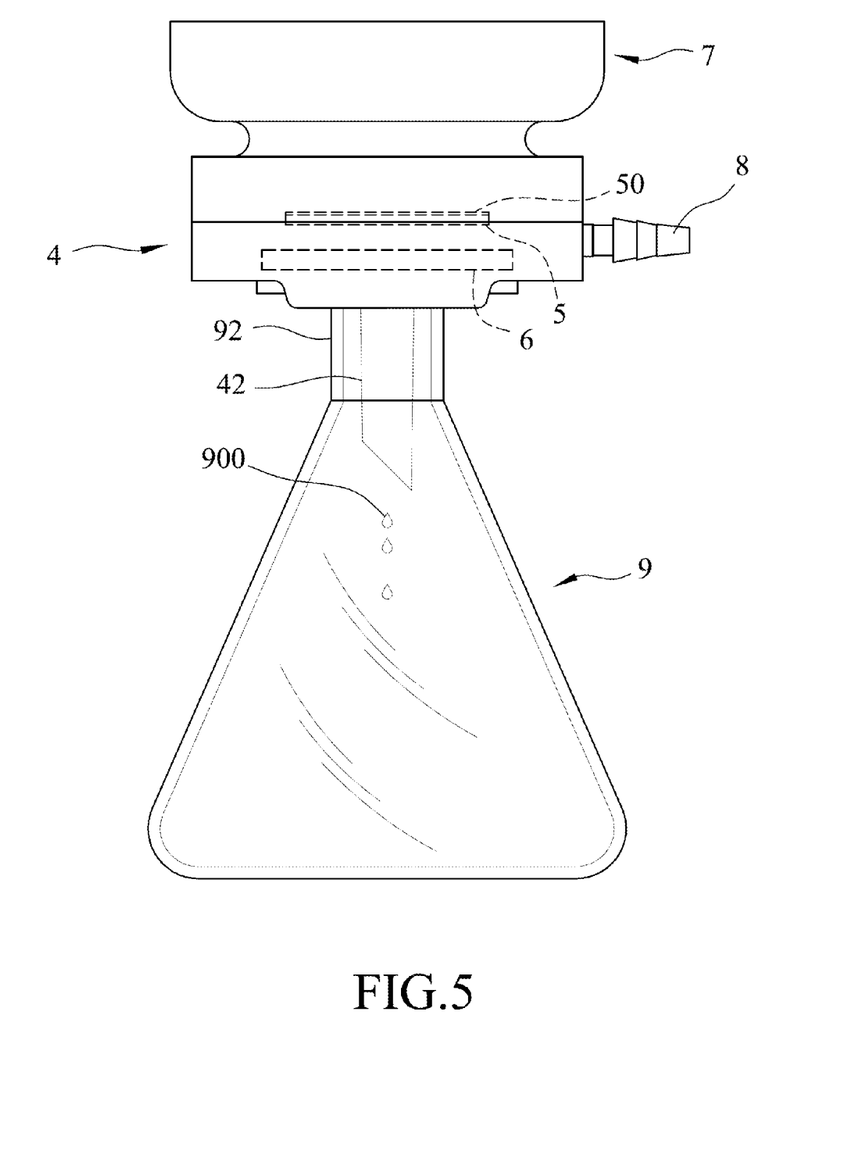
FIG. 5 is similar to FIG. 4, but illustrating the filter funnel connected to a narrow-neck flask.

It should be noted that the filter funnel of this embodiment can be connected to flasks with different flask neck sizes, as long as the seal washer 6 can fully cover the access opening 920 of the flask neck 92, and as long as the slot 62 is within the confines of the access opening 920. In FIG. 4, the filter funnel can be connected to a flask 9 with a relatively large flask neck 92. In FIG. 5, the filter funnel can be connected to a flask 9 with a relatively small flask neck 92.

Figure 6:
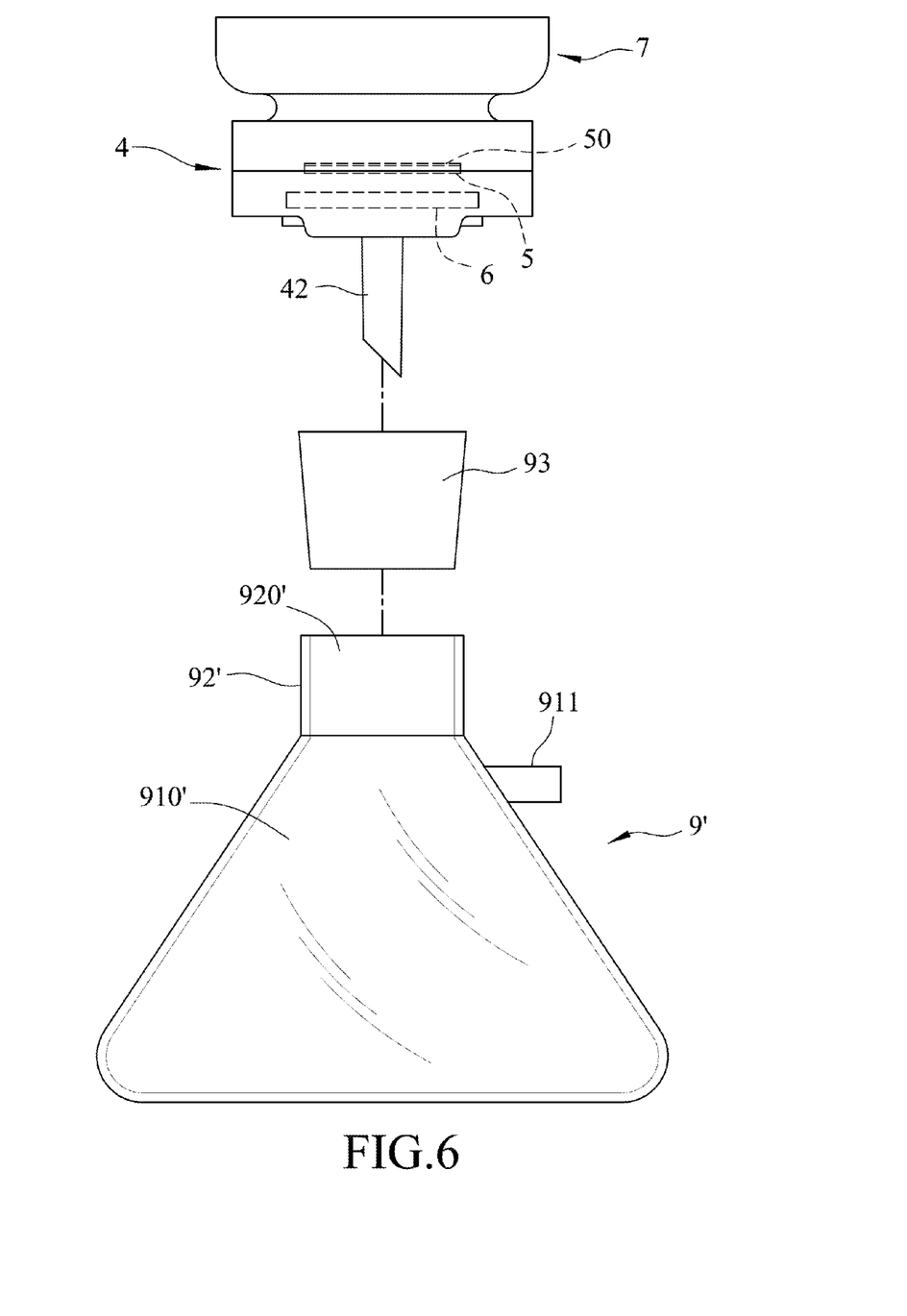
FIG. 6 illustrates the filter funnel of FIG. 1 to be connected to a Büchner flask.

With reference to FIG. 6, the filter funnel can also be connected to a Büchner flask 9' which has a hose barb 911 for connection with the source of vacuum. In this case, the tubular stem 42 is fittingly inserted into a rubber bung 93, which is inserted into an access opening 920' of a flask neck 92' of the Büchner flask 9' to ensure a vacuum tight seal between the access opening 920' and the rubber bung 93.

Figure 7:
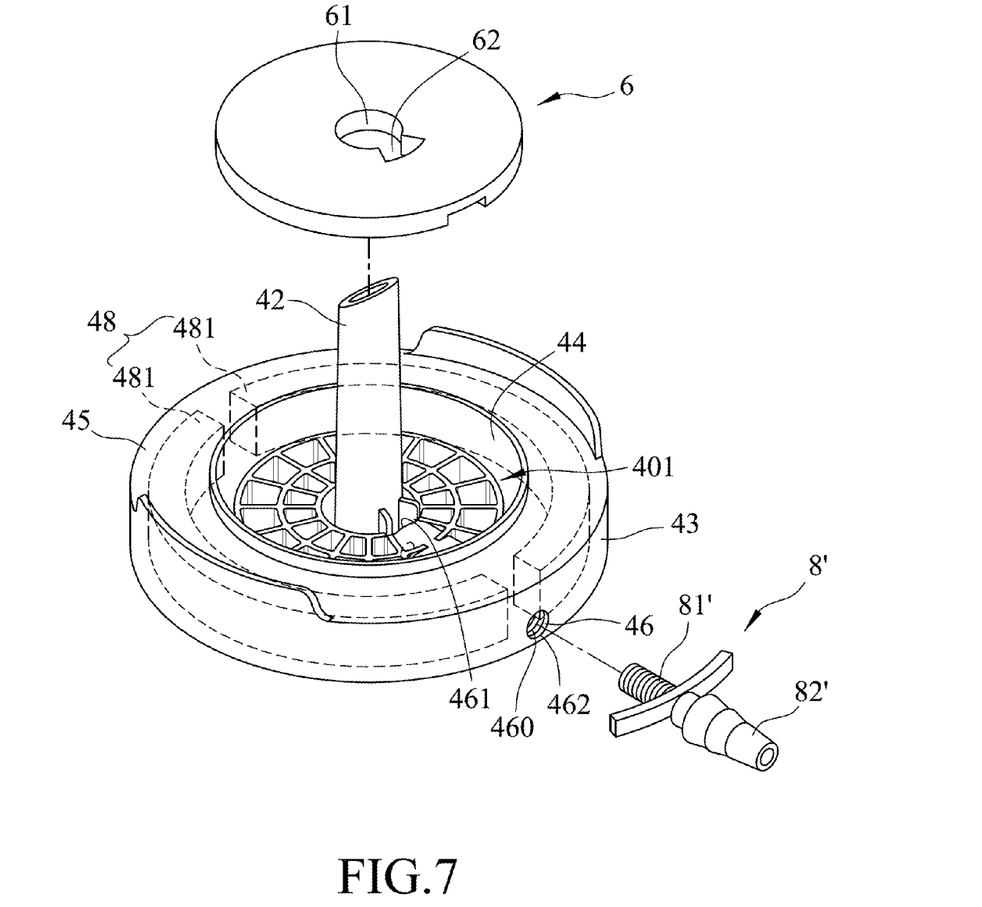
FIG. 7 is a fragmentary exploded perspective view of a second embodiment of a funnel seat according to the disclosure.
Figure 8:
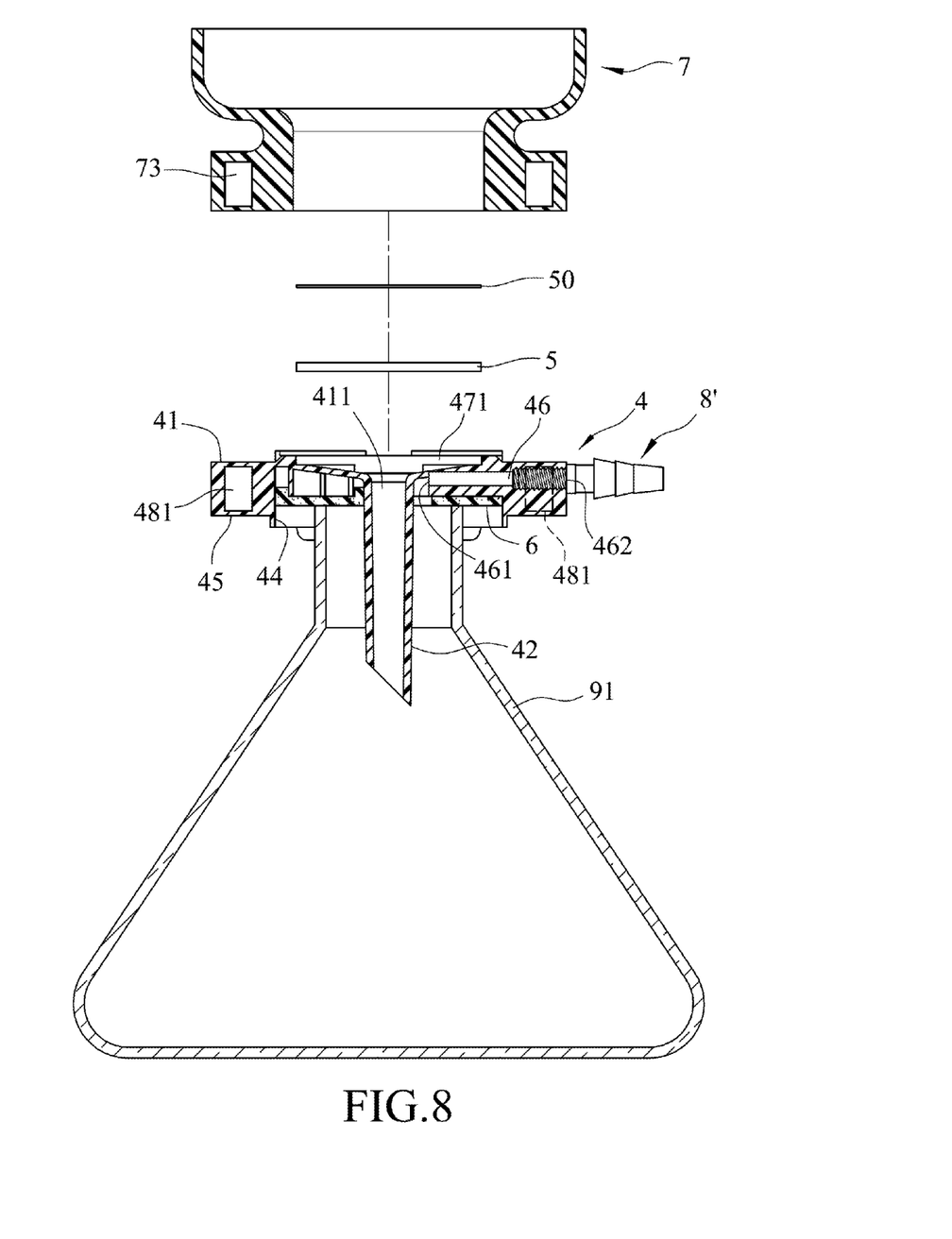
FIG. 8 is a cross-sectional view of the second embodiment of the filter funnel, in which a funnel surrounding wall is detached from a funnel seat.

FIGS. 7 and 8 show a second embodiment of a filter funnel according to the disclosure. The second embodiment is similar to the first embodiment. In the second embodiment, the vacuum intake duct 46 has a threaded region 460 disposed adjacent to the vacuum intake port 462, and a tubular connector 8' includes a threaded end 81' and a coupling end 82'. The threaded end 81' is connected with the threaded region 460 of the vacuum intake duct 46 to thereby close the vacuum intake port 462. The coupling end 82' is connected to the source of vacuum.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A filter funnel for connection to a flask which has a flask body defining an interior chamber therein, and a flask neck that has an access opening in fluid communication with the interior chamber, said filter funnel comprising:
a funnel seat having
an upper surface defining a central line and having a central surface region and a marginal surface region, said marginal surface region surrounding said central surface region,
a lower surface formed with a recess which extends from said lower surface along the central line toward said upper surface to terminate at an abutment region, said lower surface and said abutment region defining therebetween an inner surrounding surface which surrounds the central line, a through hole extending along the central line and downwardly from said central surface region to said abutment region, an outer peripheral surface which is configured to surround the central line and to join said upper surface with said lower surface, and which has a vacuum intake port, and a vacuum intake duct extending radially from said vacuum intake port to terminate at an internal port which is in fluid communication with the interior chamber of the flask body;

a funnel surrounding wall disposed on said marginal surface region of said upper surface of said funnel seat to define an accommodation space for introducing a mixture to be filtered, and a feeding inlet through which the mixture to be filtered is introduced into said accommodation space, said feeding inlet being open to an atmosphere;

a tubular stem which extends downwardly from said abutment region, and which is coaxial with and in fluid communication with said through hole so as to permit said through hole to be in fluid communication with the interior chamber of the flask body; and a seal washer having a through bore configured to permit said seal washer to be sleeved on said tubular stem so as to allow said seal washer to be brought to an attached position where said seal washer abuts against said abutment region, and a slot configured to register with said internal port when said seal washer is in the attached position such that when said seal washer is brought to cover the access opening, and when said vacuum intake port is connected to a source of vacuum, a reduced pressure is created in the interior chamber of the flask body to enable said seal washer to press against the flask neck, thereby providing an air-tight seal between the access opening and said slot, wherein said funnel surrounding wall has a bottom surrounding end surface which is detachably attached to said marginal surface region of said upper surface of said funnel seat, and wherein said filter funnel further comprises a first magnetically attractive member embedded in said bottom surrounding end surface of said funnel surrounding wall, and a second magnetically attractive member embedded in said marginal surface region of said upper surface of said funnel seat, at least one of said first and second magnetically attractive members being a magnet such that when said bottom surrounding end surface of said funnel surrounding wall is attached to said marginal surface region of said upper surface of said funnel seat, said bottom surrounding end surface and said marginal surface region are sealed by means of a magnetic attractive force generated between said first and second magnetically attractive members.

2. The filter funnel according to claim 1, wherein said funnel seat further has a plurality of rib portions which are displaced from each other in a circumferential direction, and which are disposed between said central surface region and said marginal surface region to permit said rib portions to be fitted in and to be surrounded by said funnel surrounding wall.

3. The filter funnel according to claim 1, wherein said central surface region has a plurality of guide paths each of which extends from said marginal surface region and is downwardly inclined toward said through hole so as to permit a liquid fraction of the mixture to flow toward said through hole.

4. The filter funnel according to claim 3, further comprising a mesh disc which is detachably disposed above said guide paths for supporting a filter paper.

5. The filter funnel according to claim 1, wherein said seal washer has a peripheral edge configured to be engaged with said inner surrounding surface when said seal washer is in the attached position.

6. The filter funnel according to claim 1, further comprising a tubular connector including a plug end configured to be plugged into said vacuum intake duct to close said vacuum intake port, and a coupling end configured to be connected to the source of vacuum.

7. The filter funnel according to claim 1, wherein said vacuum intake duct has a threaded region disposed adjacent to said vacuum intake port, said filter funnel further comprising a tubular connector including a threaded end configured to be connected with said threaded region of said vacuum intake duct to close said vacuum intake port, and a coupling end configured to be connected to the source of vacuum.

8. The filter funnel according to claim 1, wherein said seal washer is made of an elastomeric material.

9. The filter funnel according to claim 1, wherein said slot extends radially to communicate with said through bore.

* * * * *

UNITED STATES PATENT AND TRADEMARK OFFICE
CERTIFICATE OF CORRECTION

PATENT NO. : 9,452,373 B1  
APPLICATION NO. : 14/699814  
DATED : September 27, 2016  
INVENTOR(S) : Shui-Tien Horng Page 1 of 1

It is certified that error appears in the above-identified patent and that said Letters Patent is hereby corrected as shown below:

On the Title Page

In Item (71) Applicant, please change "Rock Scientific Co., Ltd., Kaohsiung (TW)" to --Rocker Scientific Co., Ltd., Kaohsiung (TW)--.

Signed and Sealed this  
Thirty-first Day of January, 2017

Michelle K. Lee  
*Director of the United States Patent and Trademark Office*